United States Patent
Ichilov

(10) Patent No.: US 11,826,035 B2
(45) Date of Patent: Nov. 28, 2023

(54) TREATMENT DEVICE FOR SACROILIAC JOINT HYPOMOBILITY

(71) Applicant: Pain Relief Technology, LLC, Phoenix, AZ (US)

(72) Inventor: Haddar Ichilov, Phoenix, AZ (US)

(73) Assignee: PAIN RELIEF TECHNOLOGY, LLC, Phoenix, AZ (US)

( * ) Notice: Subject to any disclaimer, the term of this patent is extended or adjusted under 35 U.S.C. 154(b) by 0 days.

(21) Appl. No.: 17/729,027

(22) Filed: Apr. 26, 2022

(65) Prior Publication Data

US 2023/0338016 A1  Oct. 26, 2023

(51) Int. Cl.
| | |
|---|---|
| A61B 17/56 | (2006.01) |
| A61B 17/58 | (2006.01) |
| A61B 17/60 | (2006.01) |
| A61B 17/02 | (2006.01) |
| A61B 17/68 | (2006.01) |
| A61F 2/30 | (2006.01) |

(52) U.S. Cl.
CPC ............ *A61B 17/025* (2013.01); *A61B 17/68* (2013.01); *A61B 2017/0256* (2013.01); *A61B 2017/564* (2013.01); *A61F 2002/30995* (2013.01); *A61F 2310/00005* (2013.01)

(58) Field of Classification Search
CPC ...................... A61B 17/025; A61B 2017/0256
See application file for complete search history.

(56) References Cited

U.S. PATENT DOCUMENTS

| | | |
|---|---|---|
| 5,626,616 A | 5/1997 | Speece |
| 8,671,482 B2 | 3/2014 | Willingham |

(Continued)

FOREIGN PATENT DOCUMENTS

| | | |
|---|---|---|
| GB | 2355664 A | 5/2001 |
| KR | 20160013230 A | 2/2016 |

(Continued)

OTHER PUBLICATIONS

PCT/US2023/019331 , "Invitation to Pay Additional Fees and, Where Applicable, Protest Fee", dated Jul. 6, 2023, 2 pages.

(Continued)

*Primary Examiner* — Christian A Sevilla
(74) *Attorney, Agent, or Firm* — Kilpatrick Townsend & Stockton LLP

(57) ABSTRACT

Treatment devices for sacroiliac (SI) joint hypomobility are described herein. In one example, a method of treating SI joint hypomobility involves positioning a person relative to a SI joint device that includes a resilient crest. Positioning the person relative to the SI joint device can involve aligning the resilient crest along the SI joint underneath the person. The method can also include using the SI joint device to pry open the SI joint. In another example, an SI joint device includes a body extending between a medial end and a lateral end, and the body includes a rigid protrusion. The SI joint device can also include a resilient cover extending over the rigid protrusion. The rigid protrusion and the resilient cover can define a crest for prying open the SI joint. The crest can include a concavity oriented towards the lateral end of the body, and the crest can deform towards the lateral end of the body when subjected to a load on a top of the crest.

17 Claims, 14 Drawing Sheets

(56) References Cited

U.S. PATENT DOCUMENTS

| | | | |
|---|---|---|---|
| 9,078,528 B2 | 7/2015 | Ramdath | |
| 9,211,230 B2 | 12/2015 | Armm | |
| 10,869,803 B1 | 12/2020 | Cohn | |
| 11,045,689 B2 | 6/2021 | Blinova | |
| 2002/0198533 A1* | 12/2002 | Geisler | A61B 17/1757 606/96 |
| 2003/0144736 A1* | 7/2003 | Sennett | A61B 17/1757 606/90 |
| 2004/0250350 A1 | 12/2004 | Leonard | |
| 2006/0010580 A1 | 1/2006 | Long | |
| 2009/0216238 A1* | 8/2009 | Stark | A61F 2/4657 606/329 |
| 2010/0262199 A1* | 10/2010 | Wallenstein | A61F 2/4611 606/86 A |
| 2014/0171835 A1 | 6/2014 | Solomon et al. | |
| 2016/0113837 A1 | 4/2016 | Burson | |
| 2016/0361603 A1 | 12/2016 | Blinova | |
| 2017/0112702 A1 | 4/2017 | Kim | |
| 2019/0231577 A1 | 8/2019 | Okamoto | |
| 2019/0388078 A1* | 12/2019 | Otto | A61B 90/06 |
| 2021/0022512 A1 | 1/2021 | Vertuca, III et al. | |
| 2021/0060287 A1 | 3/2021 | Giacomini et al. | |
| 2021/0267835 A1 | 9/2021 | DeGrandis | |
| 2021/0283003 A1 | 9/2021 | Koth | |

FOREIGN PATENT DOCUMENTS

| | | |
|---|---|---|
| KR | 101913098 B1 | 12/2018 |
| WO | 2019064321 A1 | 4/2019 |

OTHER PUBLICATIONS

PCT/US2023/019331, "International Search Report and Written Opinion," dated Aug. 30, 2023, 11 pages.

\* cited by examiner

902
Position a person relative to a SI joint device, the SI joint device comprising a resilient crest, wherein positioning the person relative to the SI joint device comprises aligning the resilient crest along the SI joint underneath the person

904
Use the SI joint device to pry open the SI joint

FIG. 9

TREATMENT DEVICE FOR SACROILIAC JOINT HYPOMOBILITY

RELATED FIELDS

This patent relates to the treatment of sacroiliac joint hypomobility, and devices and methods for the same.

BACKGROUND

Sacroiliac (SI) joints facilitate movement between the sacrum and ilium, including rotational movements (nutation and counternutation) and gliding (translational) movements. In a healthy joint, these movements are usually small (e.g., in the range of 2 mm to 4 mm and 2 degrees to 5 degrees) but are important. With hypomobility of the SI joint, the SI joint is mechanically locked-up and has reduced (if any) mobility. This can lead to a limp, lower back pain, and other problems. A person experiencing SI joint hypomobility may seek treatment to reduce pain caused by hypomobility of the SI joint. Treatment options include physical therapy including direct manipulation of the SI joint by a practitioner, surgery, and medical device interventions. Some known treatment devices for addressing SI joint hypomobility engage with the bones of the pelvis to attempt to release the SI joint. But, there remains room for improvement for treatment devices that engage directly with the hypomobile SI joint.

SUMMARY

This patent describes improved treatment devices and methods for addressing sacroiliac (SI) joint hypomobility. The devices and methods described in this patent may facilitate more efficient and effective release of a hypomobile SI joint.

In one example, a method of treating SI joint hypomobility, where the SI joint is a joint between a sacrum and ilium, involves positioning a person relative to a SI joint device, the SI joint device including a resilient crest, in which positioning the person relative to the SI joint device includes aligning the resilient crest along the SI joint underneath the person; and using the SI joint device to pry open the SI joint.

In some embodiments, the method can be performed by a medical practitioner. In other embodiments, the method can be performed by the person by himself or herself.

In some embodiments, the method can involve using the SI joint device to release one or more ligaments extending over the SI joint.

In certain embodiments, the one or more ligaments include an anterior sacroiliac ligament, a posterior sacroiliac ligament, an interosseus ligament, a sacrotuberous ligament, a sacrospinous ligament, and an iliolumbar ligament.

In some embodiments, the resilient crest is configured to deform towards the ilium as the resilient crest pries open the SI joint.

In certain embodiments, an underside of the SI joint device includes a curved surface, and using the SI joint device to pry open the SI joint further involves rocking the SI joint device.

In some embodiments, the SI joint device further includes a vibration actuator, and using the SI joint device to pry open the SI joint further involves vibrating the SI joint device.

In certain embodiments, the SI joint device includes a frame having a bottom member coupleable to a top member, and the bottom member includes a crest-shaped protrusion extendable through an opening of the top member.

In some embodiments, the resilient crest is a cover positionable over the crest-shaped protrusion. The cover can be more flexible than the frame.

In certain embodiments, the SI joint is a first SI joint of the person and the method further comprises: subsequent to using the SI joint device to pry open the first SI joint, positioning the person relative to the SI joint device by aligning the resilient crest along a second SI joint underneath the person; and using the SI joint device to pry open the second SI joint.

In another example, an SI joint device for treating SI joint hypomobility includes: a body extending between a medial end and a lateral end and, the body having a rigid protrusion and a resilient cover extending over the rigid protrusion. The rigid protrusion and the resilient cover define a crest configured to pry open an SI joint. The crest includes a concavity oriented towards the lateral end of the body. The crest is configured to deform towards the lateral end of the body when subjected to a load on a top of the crest.

In some embodiments, the body includes an upper surface and a lower surface. The rigid protrusion and the resilient cover are located at the upper surface. The lower surface includes a curvature configured to facilitate rocking of the SI joint device.

In certain embodiments, the crest extends along a generally superior-inferior axis of the SI joint device.

In some embodiments, the lateral end of the body is narrower than the medial end.

In certain embodiments, the rigid protrusion comprises a crest-shape protrusion.

In some embodiments, the SI joint device includes a vibration actuator configured to vibrate the SI joint device to pry open the SI joint.

In certain embodiments, the vibration actuator is configured to be positioned within an internal cavity of the rigid protrusion.

In some embodiments, the body includes a bottom cover configured to be positioned over the internal cavity.

The body includes a top member and a bottom member configured to be coupled via a coupling mechanism.

BRIEF DESCRIPTION OF DRAWINGS

FIG. 9 is a flowchart of an example of a method for treating SI joint hypomobility using an SI joint device.

DETAILED DESCRIPTION

Figure 1A:
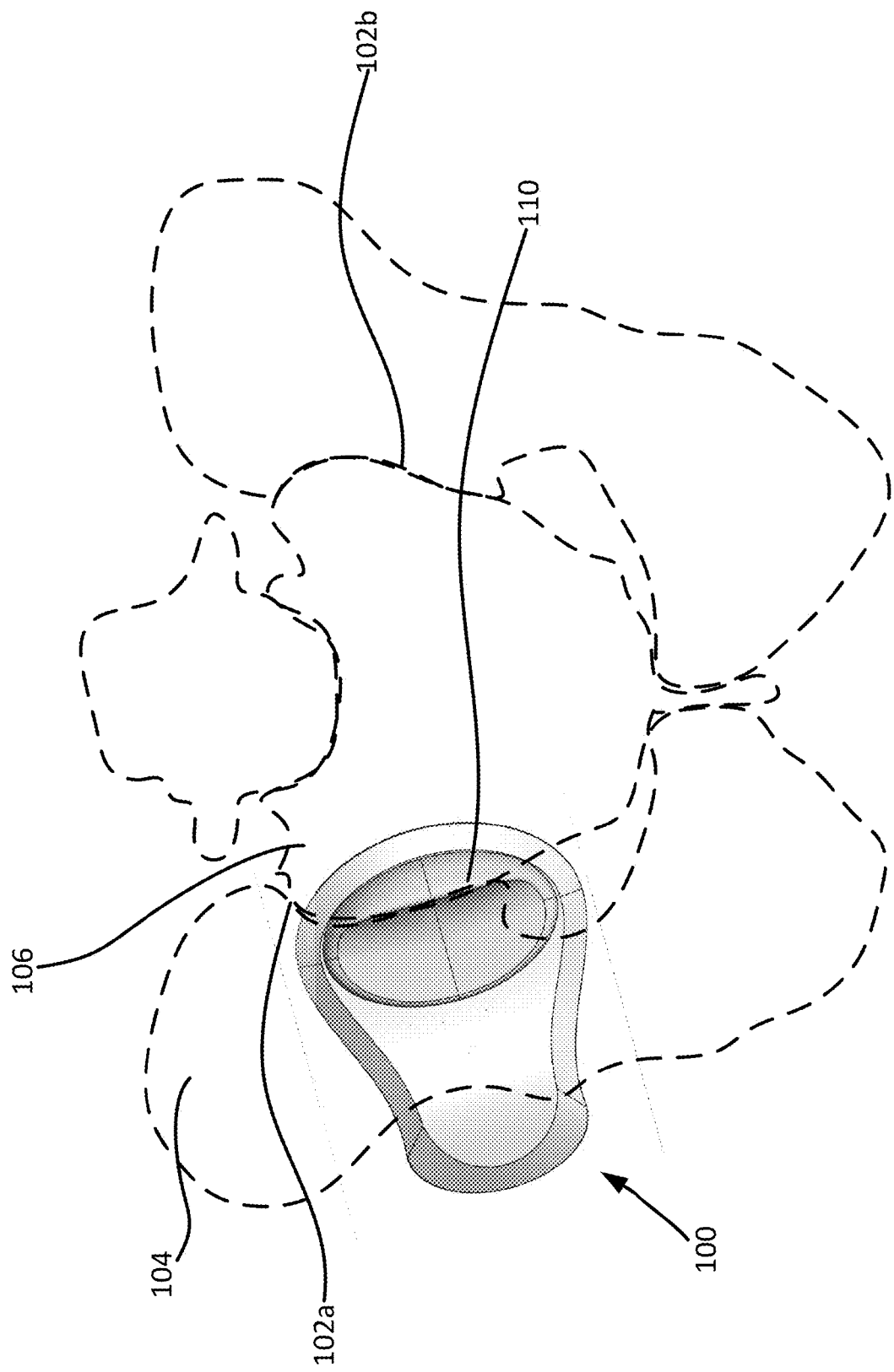
FIGS. 1A-1C illustrates an example of a sacroiliac (SI) joint device positioned relative to left (FIGS. 1A-B) and right (FIG. 1C) SI joints.

FIG. 1A shows an example of a sacroiliac (SI) joint device 100 positioned relative to an SI joint 102a. The SI joint 102a is between a sacrum 106 and an ilium 104 of a person, and each person has two SI joints 102a-b. The sacrum 106 is medial and the ilium 104 is lateral. The SI joint device 100 can be positioned underneath the person so that a resilient crest 110 of the SI joint device 100 is aligned along the SI joint 102a. The resilient crest 110 can deform towards the ilium 104 to pry open the SI joint 102a when subjected to a load, with the load being either the person's own body weight or the person's own body weight combined with a downward force applied by a practitioner.

Figure 1B:
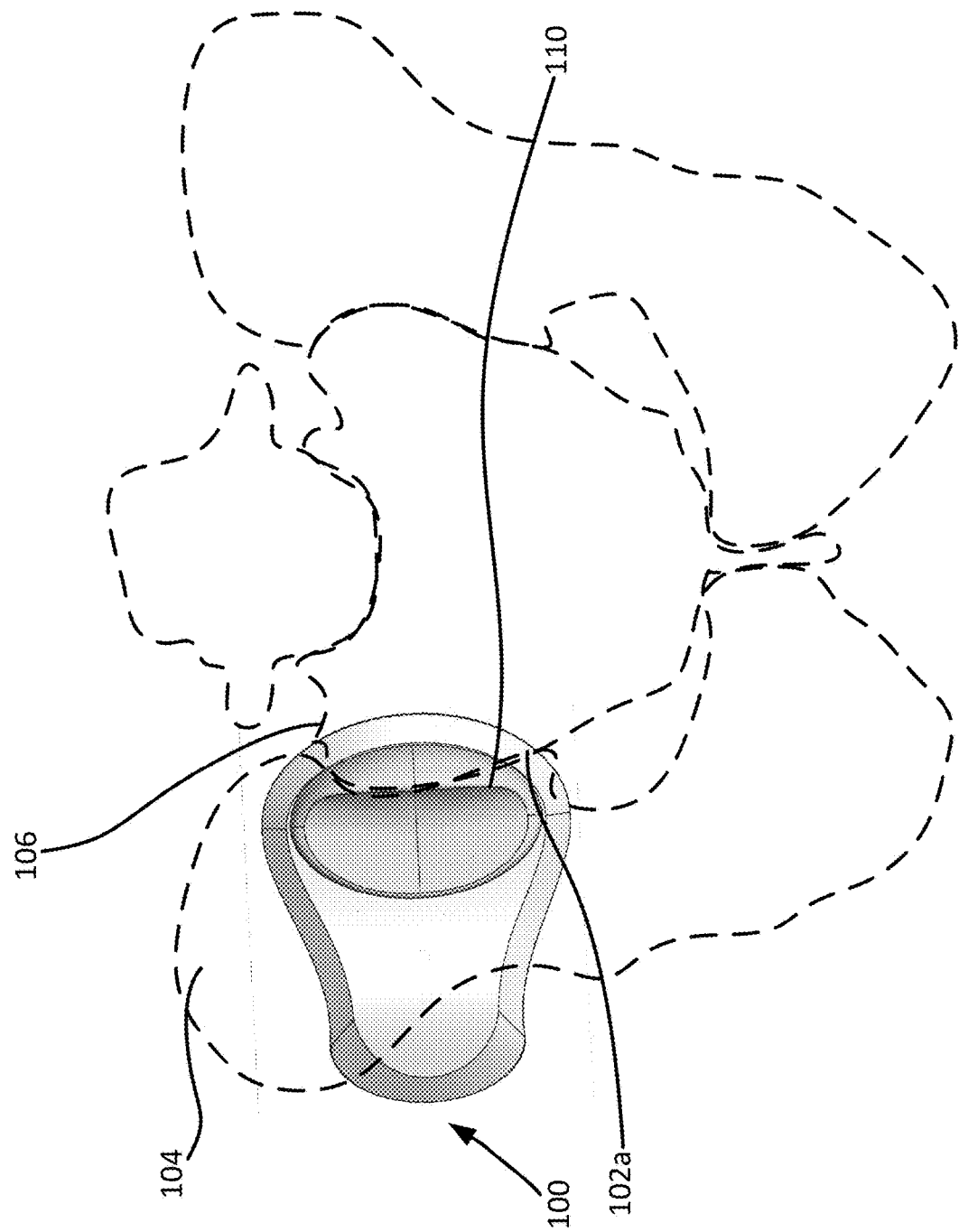
Figure 1C:
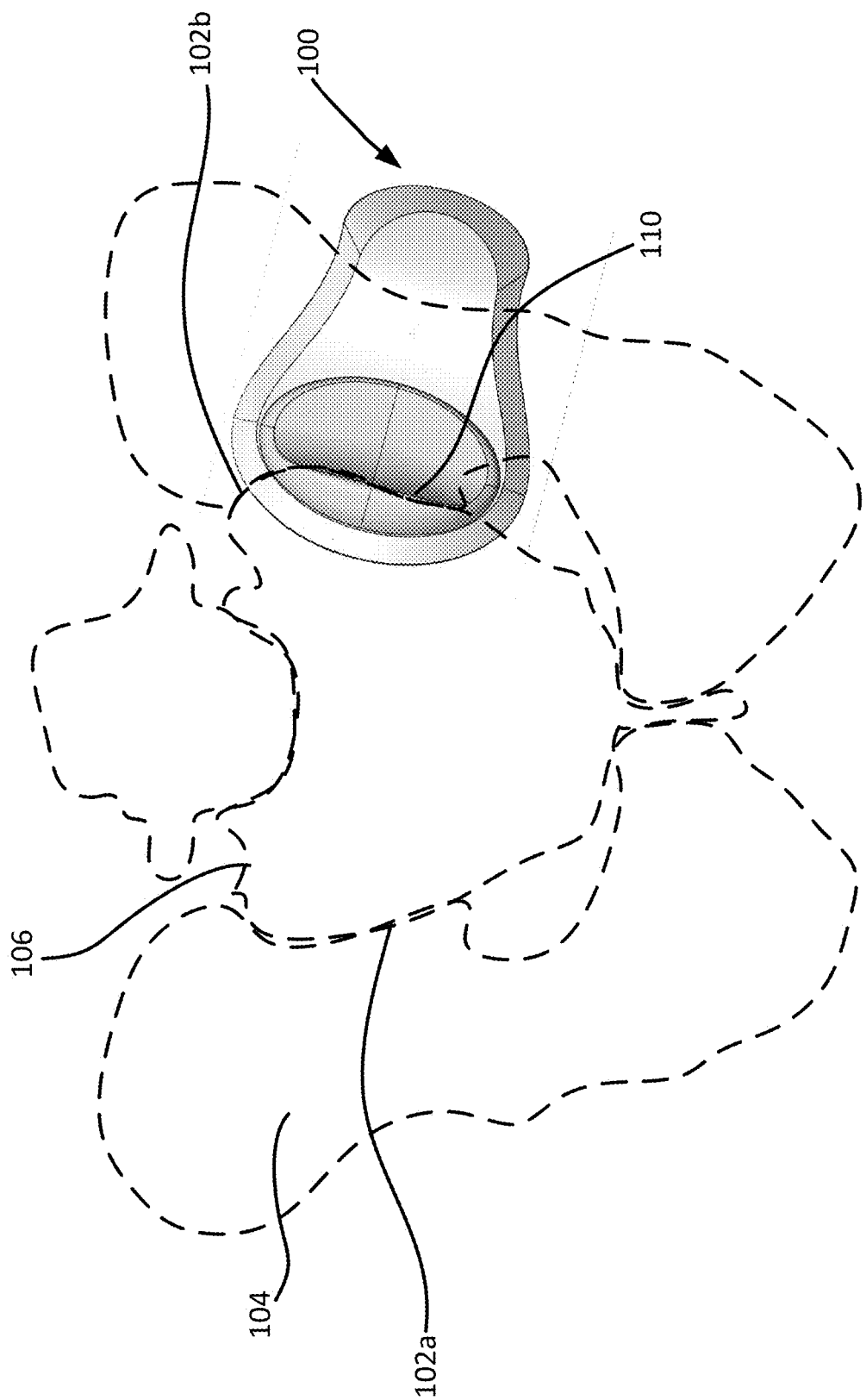

The SI joint device 100 can be repositioned along the SI joint 102a to pry open the SI joint 102a at different locations, as illustrated in FIGS. 1A and 1B. The SI joint device 100 can be oriented at a different angle at the different locations so that the resilient crest 110 remains aligned along the SI joint 102a. In addition to being positioned at various locations of the SI joint 102a, the SI joint device 100 can also be moved to the other side of the person to pry open the other SI joint 102b, as illustrated in FIG. 1C. The SI joint device 100 may be moved to the other side after the SI joint device 100 is used to pry open the SI joint 102a. The resilient crest 110 can be aligned along the other SI joint 102 at various locations and at various angles, with the resilient crest 110 generally aligned along the SI joint.

Figure 2:
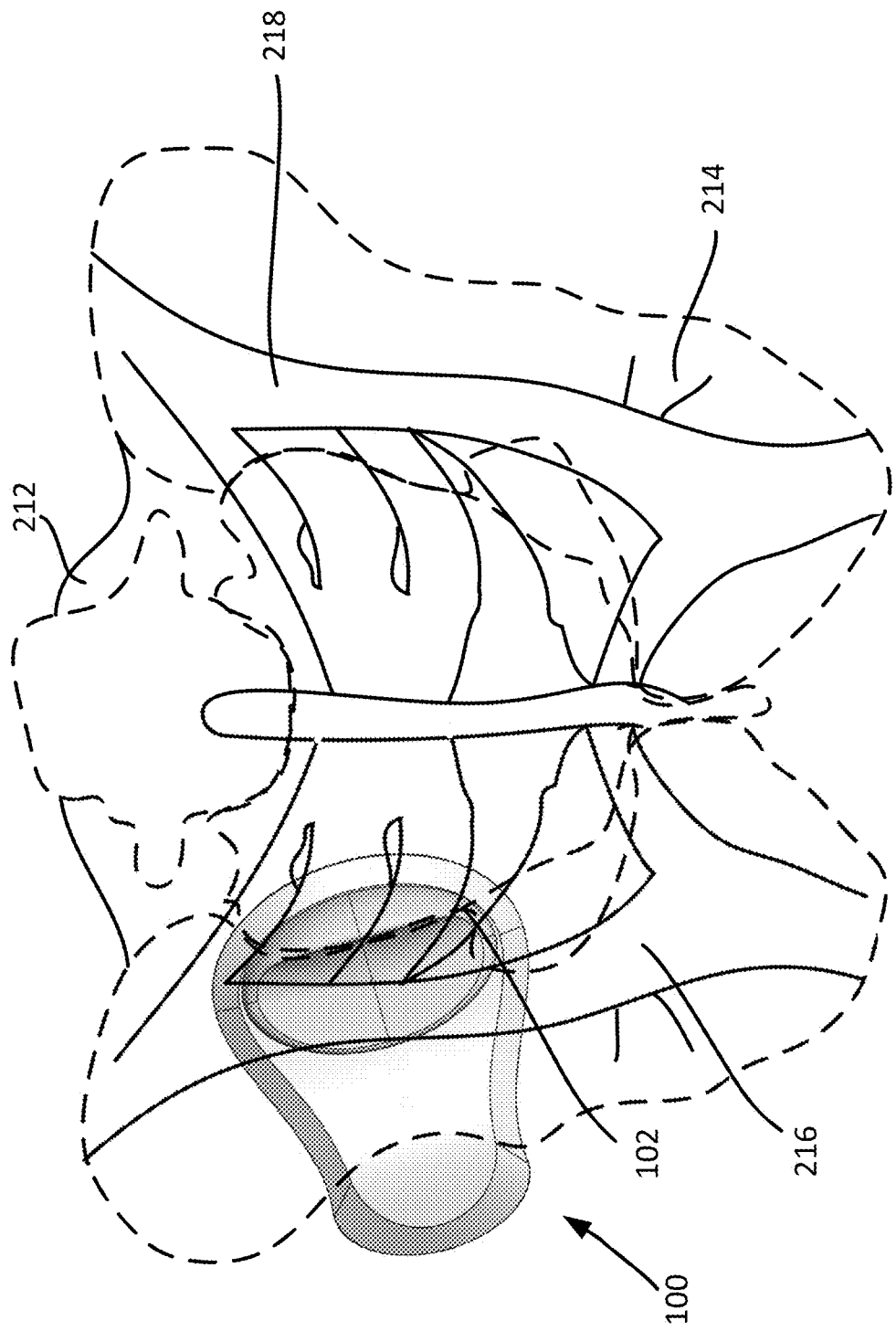
FIG. 2 illustrates an SI joint device positioned with respect to ligaments extending over an SI joint, the ligaments being between the SI joint device and the SI joint.

FIG. 2 schematically illustrates an SI joint device 100 positioned with respect to ligaments extending over an SI joint 102. In FIG. 2, the patient is lying on his or her back, with the SI joint device 100 positioned underneath, and the ligaments of interest are between the SI joint device 100 and the SI joint 102. With the resilient crest of the SI joint device 100 aligned along the SI joint 102, and downward force applied, the SI joint device 100 can release one or more of an iliolumbar ligament 212, a sacrospinous ligament 214, a sacrotuberous ligament 216, a posterior sacroiliac ligament 218, an interosseous ligament (not shown) underneath the posterior sacroiliac ligament 218, and an anterior sacroiliac ligament (not shown). Aligning the SI joint device 100 at different locations of the SI joint 102 may result in a release of different ligaments. For instance, aligning the SI joint device 100 along a lower portion of the SI joint 102 may result in a release of the sacrospinous ligament 214 and the sacrotuberous ligament 216, whereas aligning the SI joint device 110 along an upper portion of the SI joint 102 may result in a release of the posterior sacroiliac ligament 218, the anterior sacroiliac ligament, the interosseous ligament, and the iliolumbar ligament 212.

Releasing a ligament can be a reduction of ligament tension. Ligaments may be a significant source of pain, especially in cases of chronic pain. Until injured ligaments can heal from their underlying dysfunction, muscles remain in a tense and guarded state, which leads to reduced function and increased pain. Muscles that can add tension to the sacrotuberous ligament 216 include the gluteus maximus, the hamstrings, and possibly the piriformis, since each of these muscles have direct attachments to the sacral ligaments. There are also a number of muscles that are used to create movement at the sacrum that can also add tension to the sacral ligaments. These muscles include the spinal erectors, in particular the lumbar multifidii, which extends into the sacral region, the obturator internus and gemelli, quadratus femoris, the lower band of the transverse abdominus and sartorius.

The SI joint device 100 can stimulate cells in the ligaments called mechanoreceptors. The job of mechanoreceptors is to make sure the SI joint 102 is stable by monitoring the SI joint 102 via the tensions felt on the ligaments. When these cells sense instability in the SI joint 100, they send a signal to the surrounding muscles to tighten themselves and stabilize the SI joint 100. So, when there is chronic ligament damage, muscles become stuck in a pattern of spasms. If the ligament remains in this condition, the muscles are constantly activated keeping up the tension to stabilize the SI joint 100 by taking the load off the ligaments. By gently stimulating these mechanoreceptors, the SI joint device 100 manipulates the sensory output to the muscles, tendons, and fascia, which results in the reduction of ligament tension.

Figure 3A:
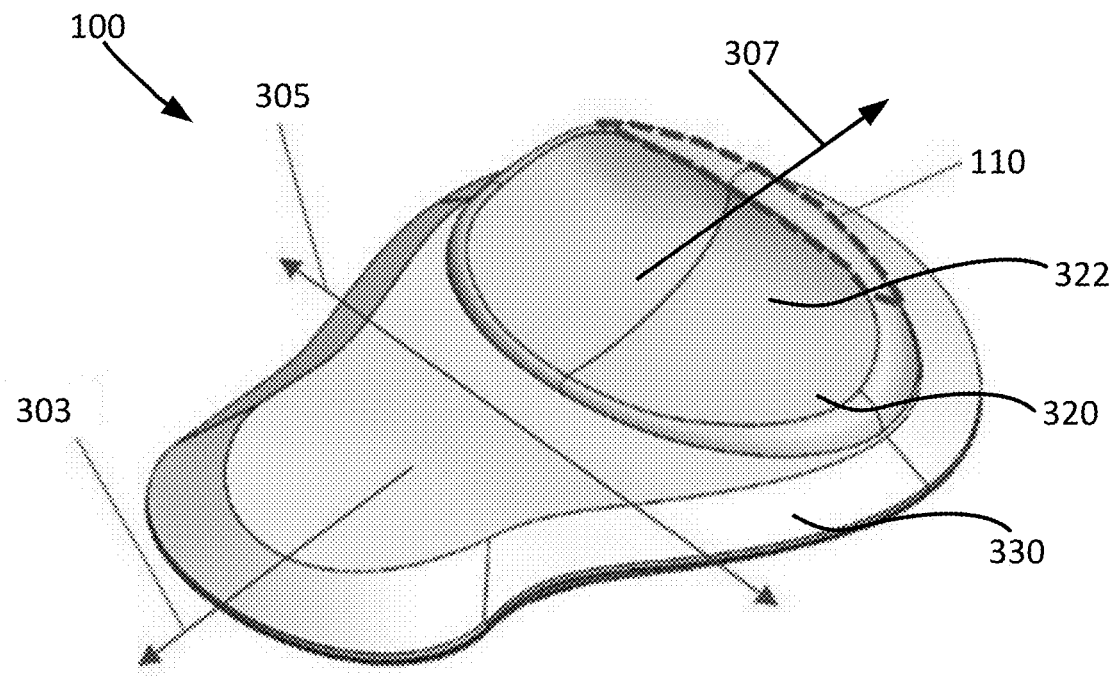
FIGS. 3A-3B shows one example of an SI joint device, with FIG. 3B showing a cover of the device removed.

FIGS. 3A-3B, 4A-4B, and 5A-5B show one example of an SI joint device 100 from various views. As illustrated in FIG. 3A, the SI joint device 100 includes a resilient cover 320 that includes the resilient crest 110. The resilient cover 320 can be positioned over a body 330 of the SI joint device 100. The resilient cover 320 can be made of silicone and be more flexible than the body 330, which may be made of metal or plastic. The body 330 can be substantially an oval shape extending from a lateral end 303 to a medial end 307. The lateral end 303 of the body 330 can be narrower than the medial end 307.

In the example shown, the resilient cover 320 is positioned over a rigid protrusion 332 at the medial end 307 of the body 330. The resilient crest 110 of the resilient cover 320 can generally extend along a superior-inferior axis 305 of the SI joint device 100 ("generally" refers to the gentle curvature of the crest). The resilient crest 110 is associated with a concavity 322 of the cover 320 oriented towards the lateral end 303 of the device 100, such that when a top of the resilient crest 110 is subjected to a load, the resilient crest 110 can deform towards the lateral end 303 (see for example FIG. 8 discussed further below).

Figure 3B:
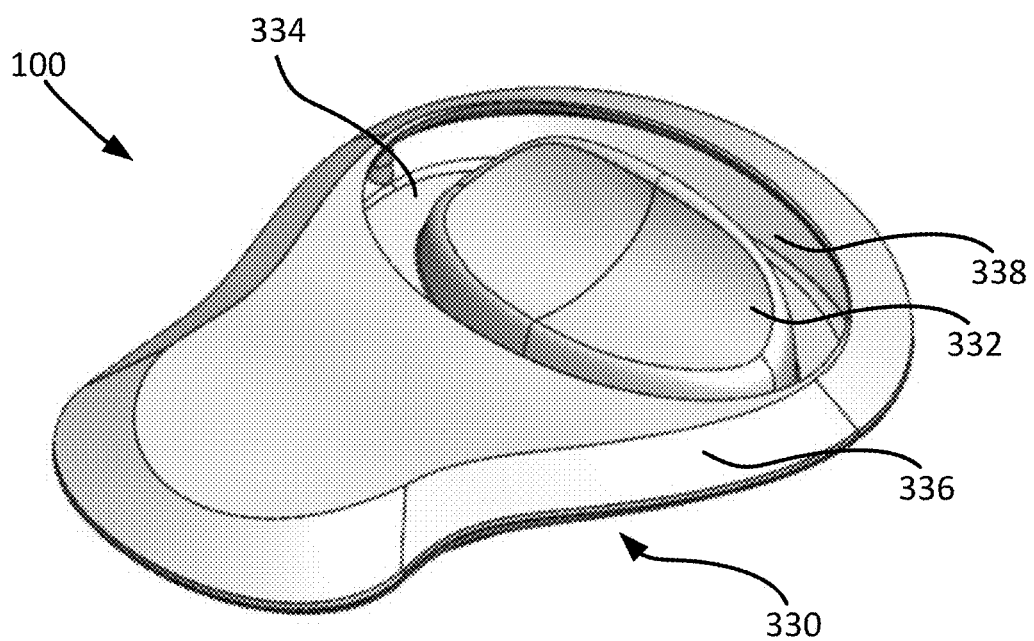
Figure 4B:
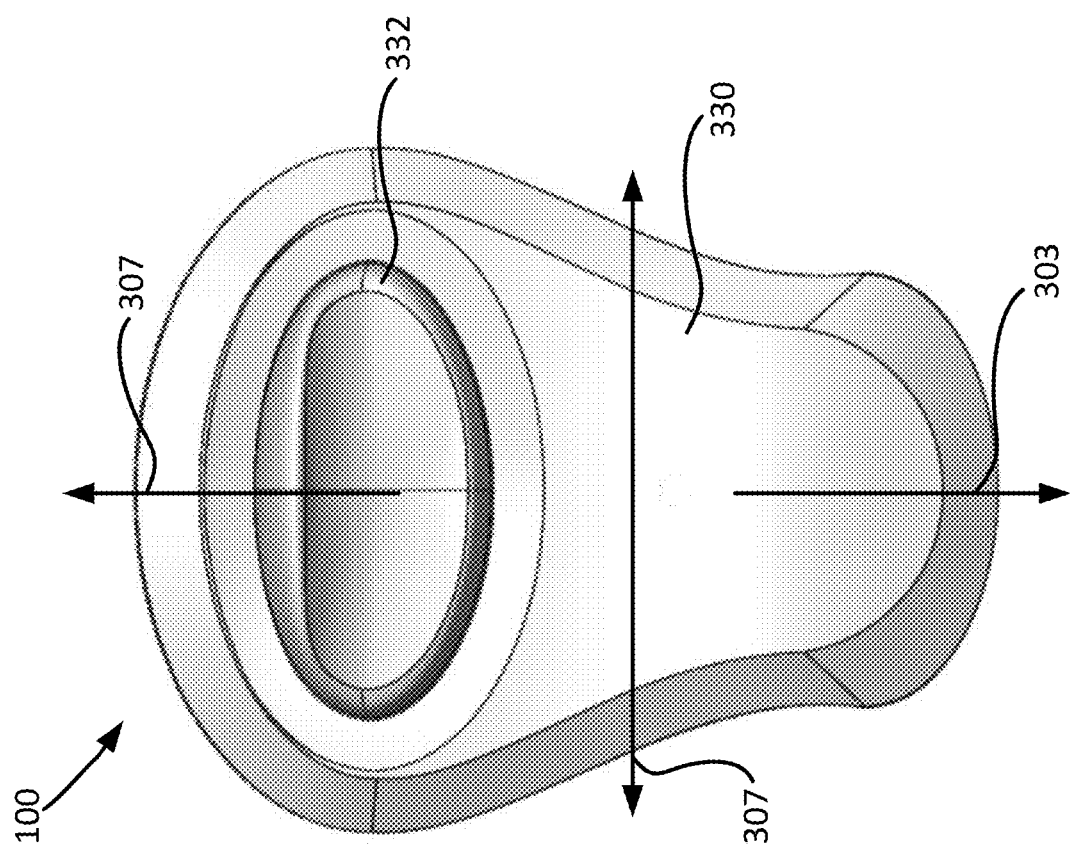
FIGS. 4A-4B show the device of FIGS. 3A-B from a top view.
Figure 4A:
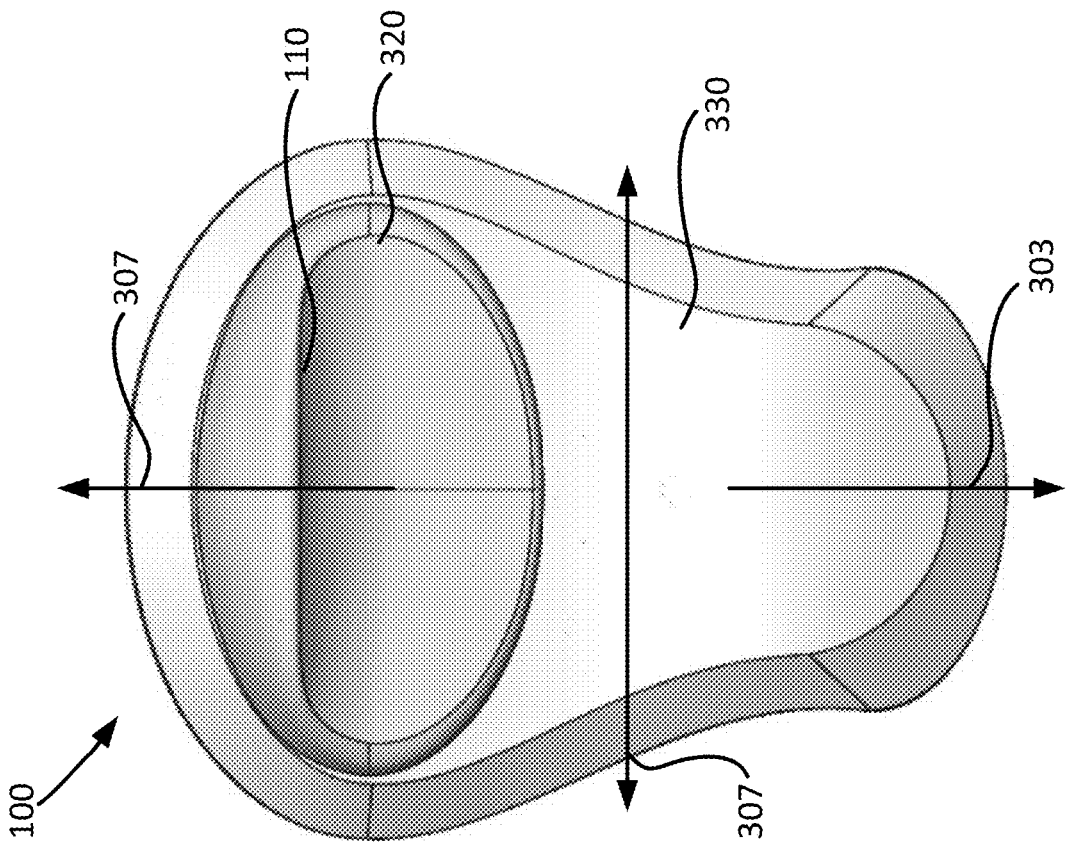

As shown in FIG. 3B, the rigid protrusion 332 may also include a crest-shaped protrusion corresponding to the resilient crest 110 of the resilient cover 320. But, in other examples the rigid protrusion 332 may not be crest-shaped.

Figure 5A:
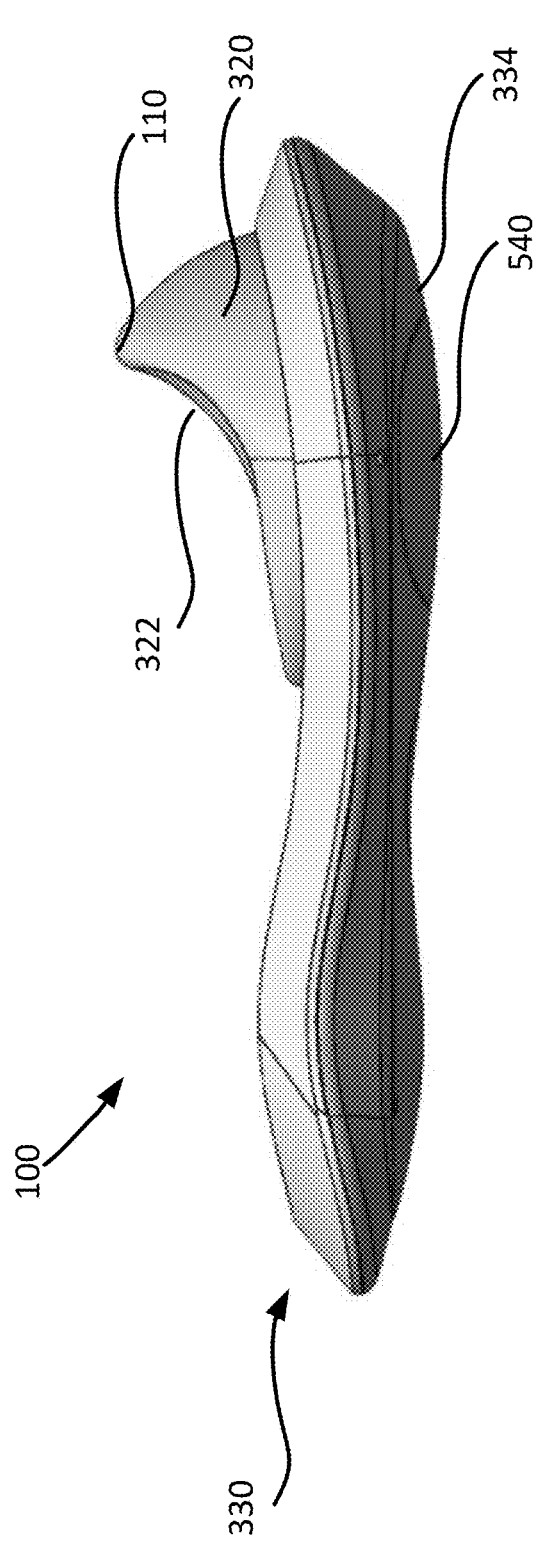
FIGS. 5A-5B show the device of FIGS. 3A-B from a side view.
Figure 5B:
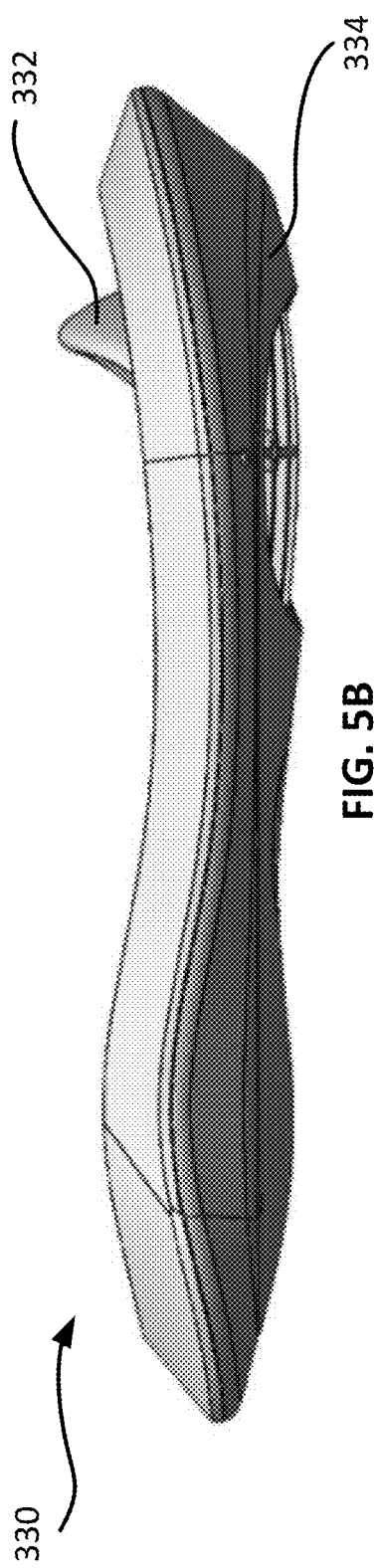

As shown in FIGS. 5A-B, the body 330 can include a bottom member 334 coupled to a top member 336. The bottom member 334 can be a lower surface of the body 330 and the top member 336 can be an upper surface of the body 330. The rigid protrusion 332 and the resilient cover 320 can be located at and extend from the upper surface when the device is assembled. As best shown in FIG. 7B, the rigid protrusion 332 can extend through an opening 338 of the top member 336. The opening 338 can be an oval-shaped opening oriented along the superior-inferior axis 305 at the medial end 307.

The SI joint device 100 can be positioned underneath a person, with the resilient crest 110 aligned along an SI joint of the person. The medial end 307 can be positioned medially with respect to the person and the lateral end 303 can be positioned laterally with respect to the person. In some instances, at least a portion of the lateral end 303 may extend beyond the person. When subjected to a load, such as the body weight of a person, the resilient crest 110 can deform towards a lateral end 303 of the body 330 to pry open the SI joint. As the resilient crest 110 deforms, the resilient crest 110 can grip and pull an iliac surface away from a sacral surface of the SI joint because of the force downward and the angle of the resilient crest 110.

FIGS. 6A-6D illustrate bottom views of an SI joint device 100. The bottom member 334 can be coupled to the top member (e.g., top member 336 in FIG. 3B) via a coupling mechanism 642. In FIGS. 6A-6D, the coupling mechanism 642 is illustrated as a countersunk screw, but the coupling mechanism 642 may alternatively be a snap-fit mechanism, an epoxy coupling, etc. The coupling mechanism 642 can be configured so that the coupling mechanism 642 does not interfere with the curvature of the bottom member 334.

Figure 6A:
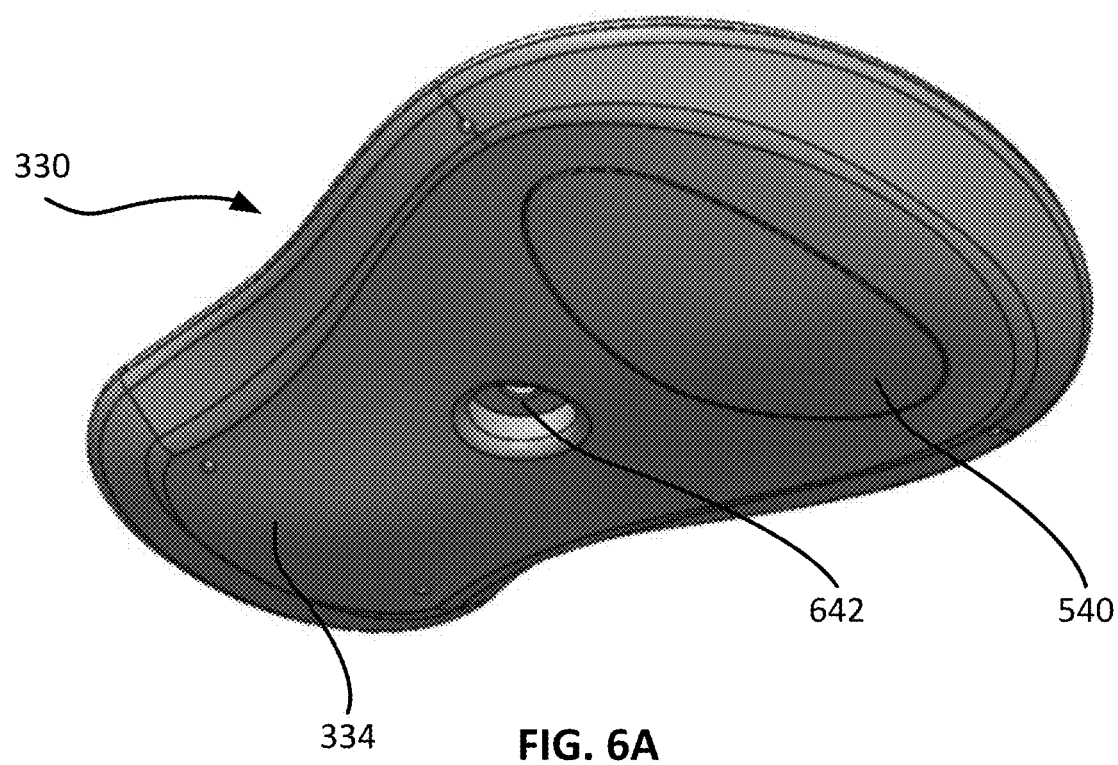
FIGS. 6A-6D show the device of FIGS. 3A-B from bottom views, with FIGS. 6B and 6D showing the device with a bottom cover removed.
Figure 6B:
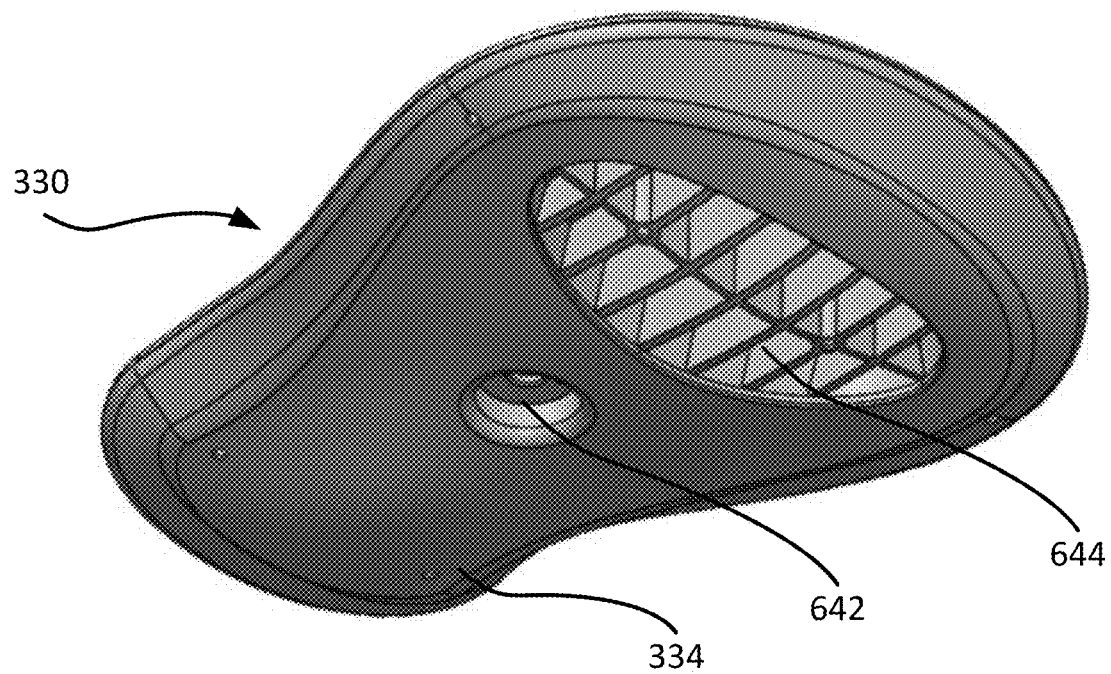
Figure 6C:
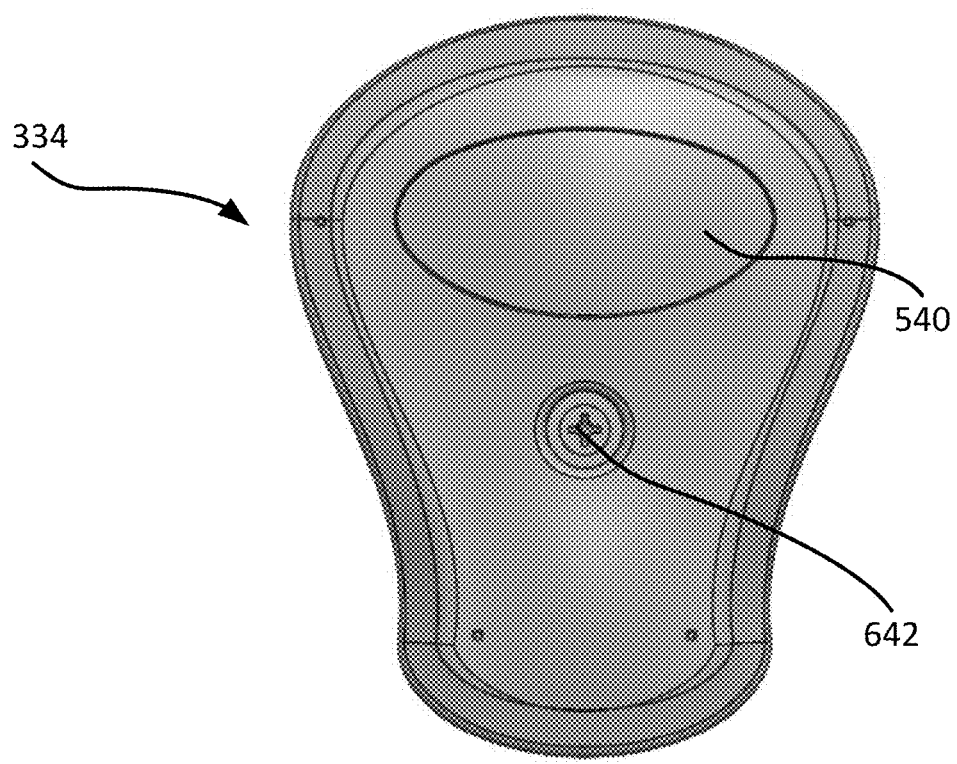
Figure 6D:
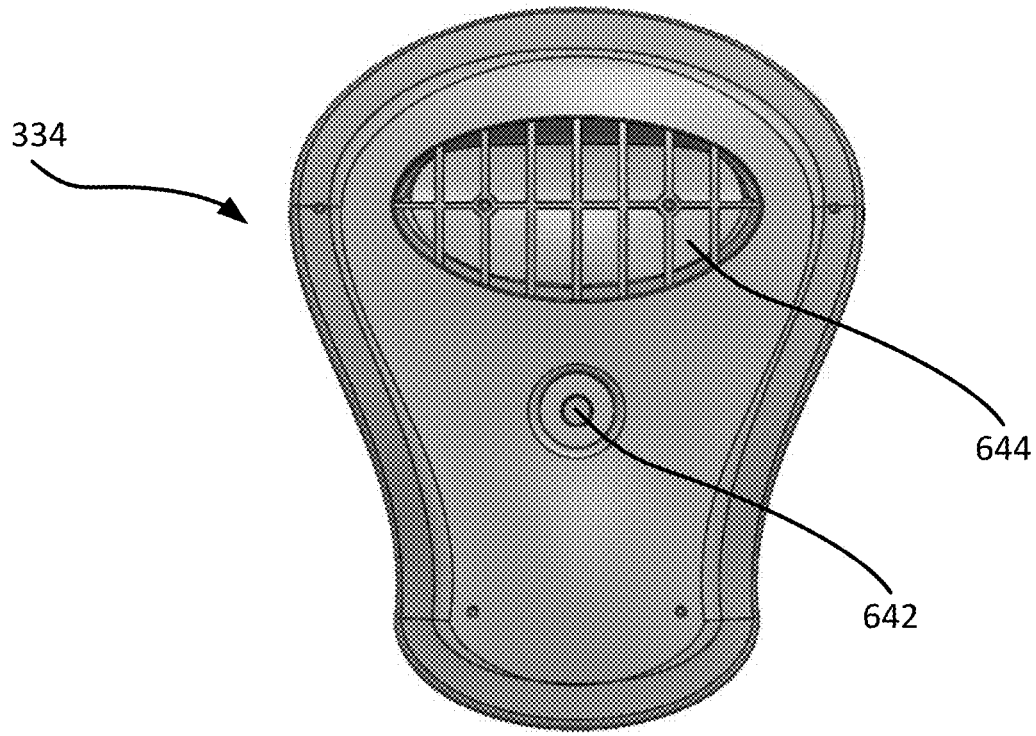

The bottom member 334 includes the bottom cover 540 in FIGS. 6A and 6C. When the bottom cover 540 removed, as shown in FIGS. 6B and 6D, an internal cavity 644 of the body 330 may be at least partially hollow to reduce an amount of material used in manufacturing the SI joint device 100. In addition, and as described below, the SI joint device 100 may include a vibration actuator positioned within the internal cavity 644 for rocking the SI joint device.

In FIGS. 5A and 6A, the bottom member 334 of the body 330 is illustrated as including a curved surface. The curved surface can facilitate rocking of the SI joint device 100 to help mechanically release the SI joint and ligaments extending over the SI joint. Although not shown, the SI joint device 100 can be modified to include a vibration actuator, which during use can be actuated to vibrate the SI joint device 100, helping to release the SI joint. The vibration actuator may be placed inside a cavity of the rigid protrusion 332 of the body 330. For instance, the rigid protrusion 332 may be hollow, and the bottom member 334 can include a bottom cover 540 that be removed so that the vibration actuator can be placed within the rigid protrusion 332. The bottom cover 540 can then be coupled back into place to secure the vibration actuator within the body 330. The bottom cover 540 may be coupled to the bottom member 334 via a snap-fit mechanism, a screw, or other suitable attachment mechanism. In the example shown in the figures, the device does not include a vibration actuator, and the cavity inside the rigid protrusion 332 is instead filled with reinforcement ribs, as shown best in FIG. 6B.

Figure 7A:
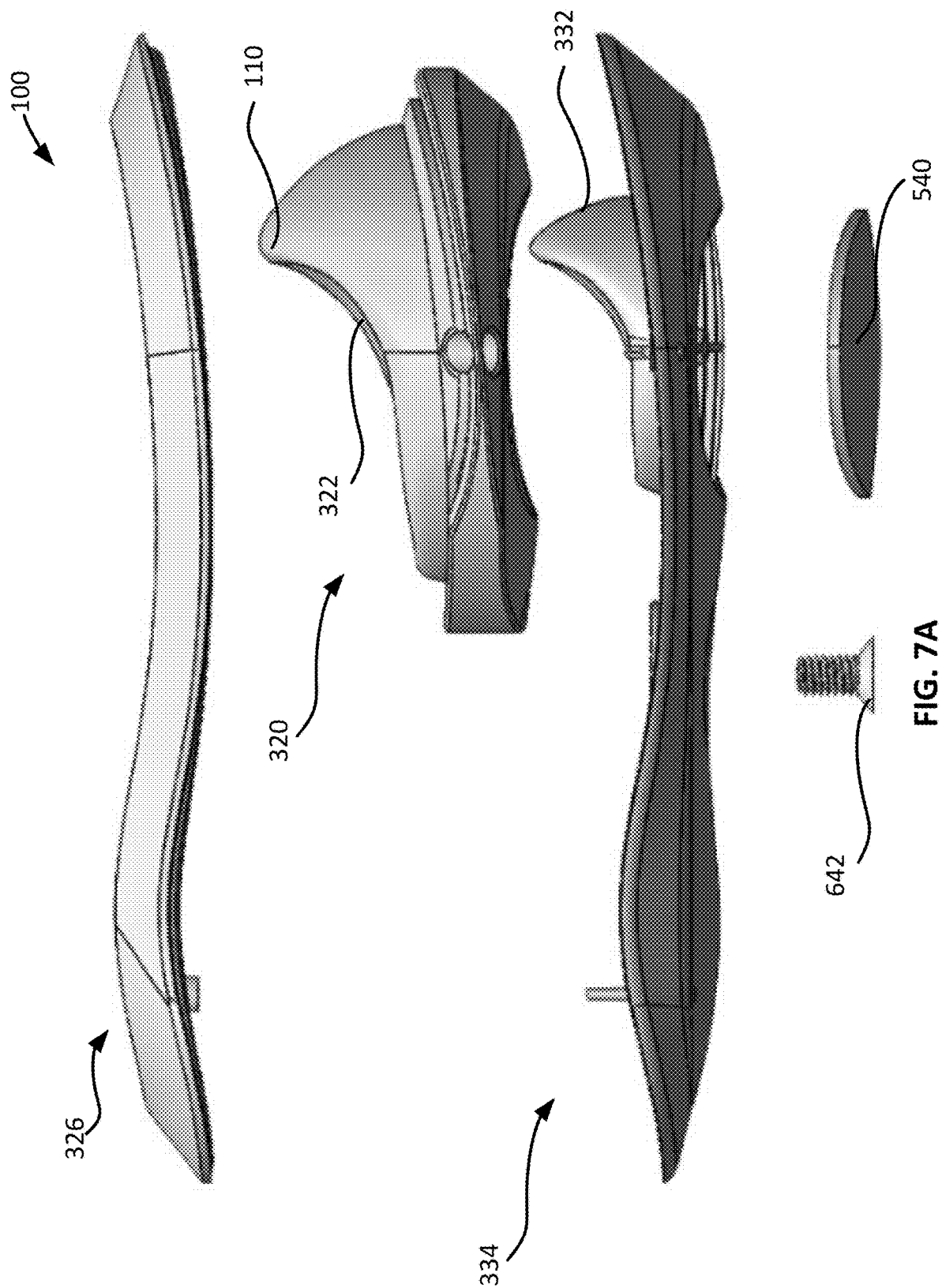
FIGS. 7A-7C are exploded views of the device of FIGS. 3A-B.
Figure 7B:
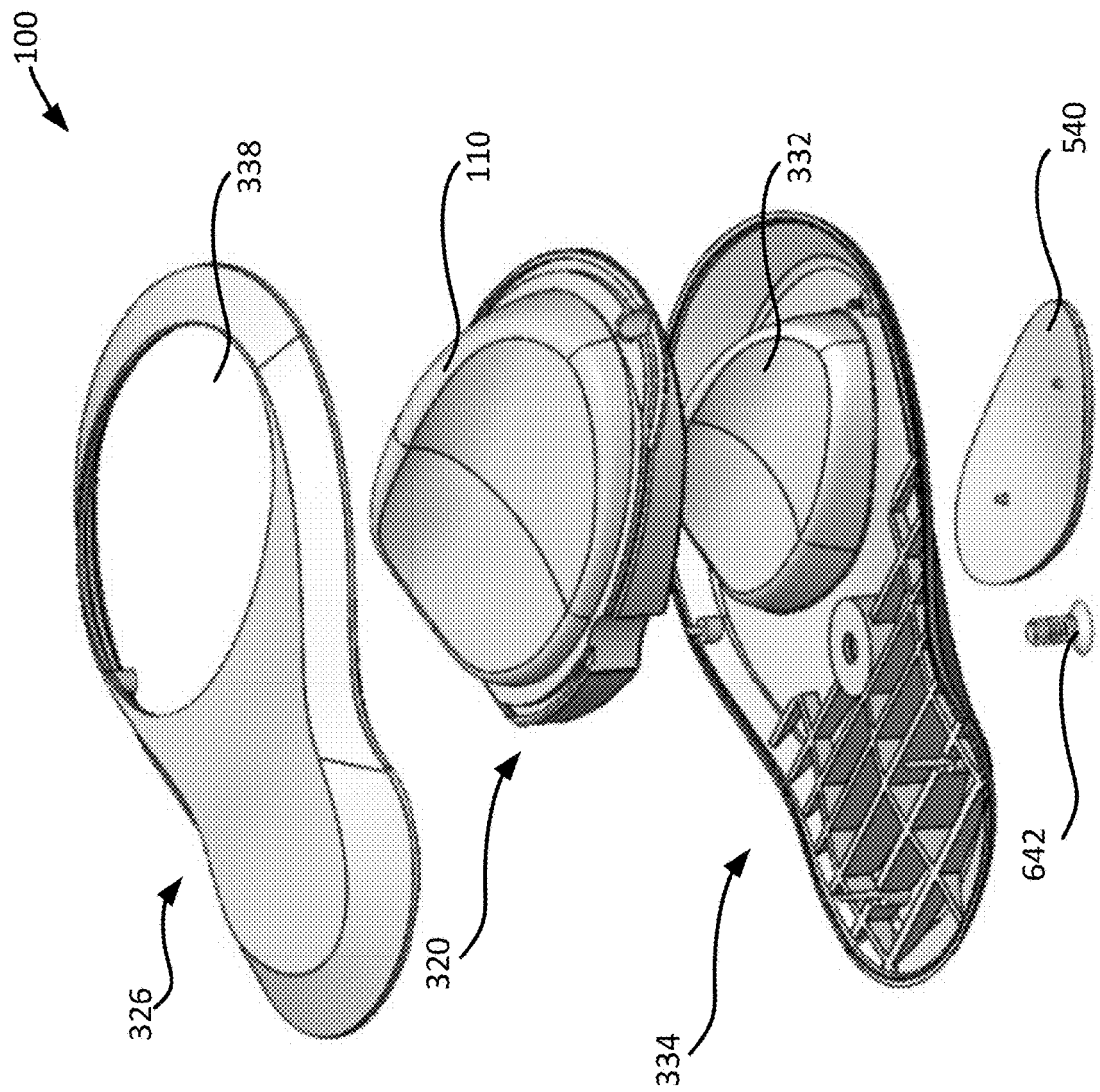
Figure 7C:
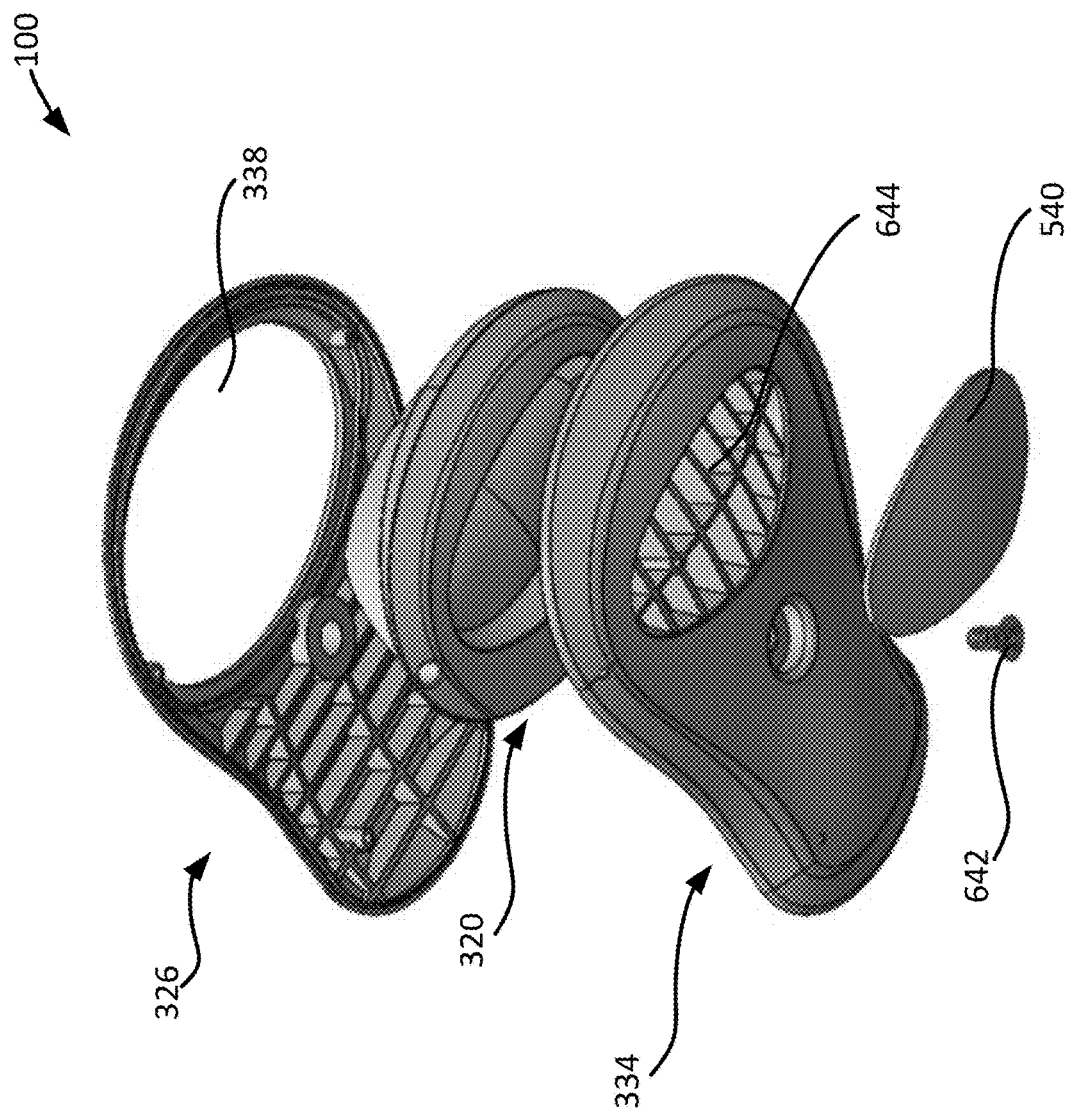

FIGS. 7A-7C illustrate exploded views of an SI joint device 100. The SI joint device 100 can include a top member 326 with an opening 338, through which a rigid protrusion 332 of a bottom member 334 can extend. The top member 326 can be coupled to the bottom member 334 and form a body of the SI joint device 100. The resilient cover 320 can be positioned over the rigid protrusion 332 via a coupling mechanism 642. The rigid protrusion 332 and the resilient cover 320 can define a crest, corresponding to resilient crest 110. The resilient crest 110 can include a concavity 322 oriented towards a lateral end of the body, and the resilient crest 110 can deform towards the lateral end of the body when subjected to a load on top of the resilient crest 110. In addition, the bottom member 334 can be a lower surface of the body that includes a curvature for facilitating rocking of the SI joint device 100. The bottom member 334 can include a bottom cover 540 that can be removable for insertion of a vibration actuator into an internal cavity 644 of the body.

Figure 8:
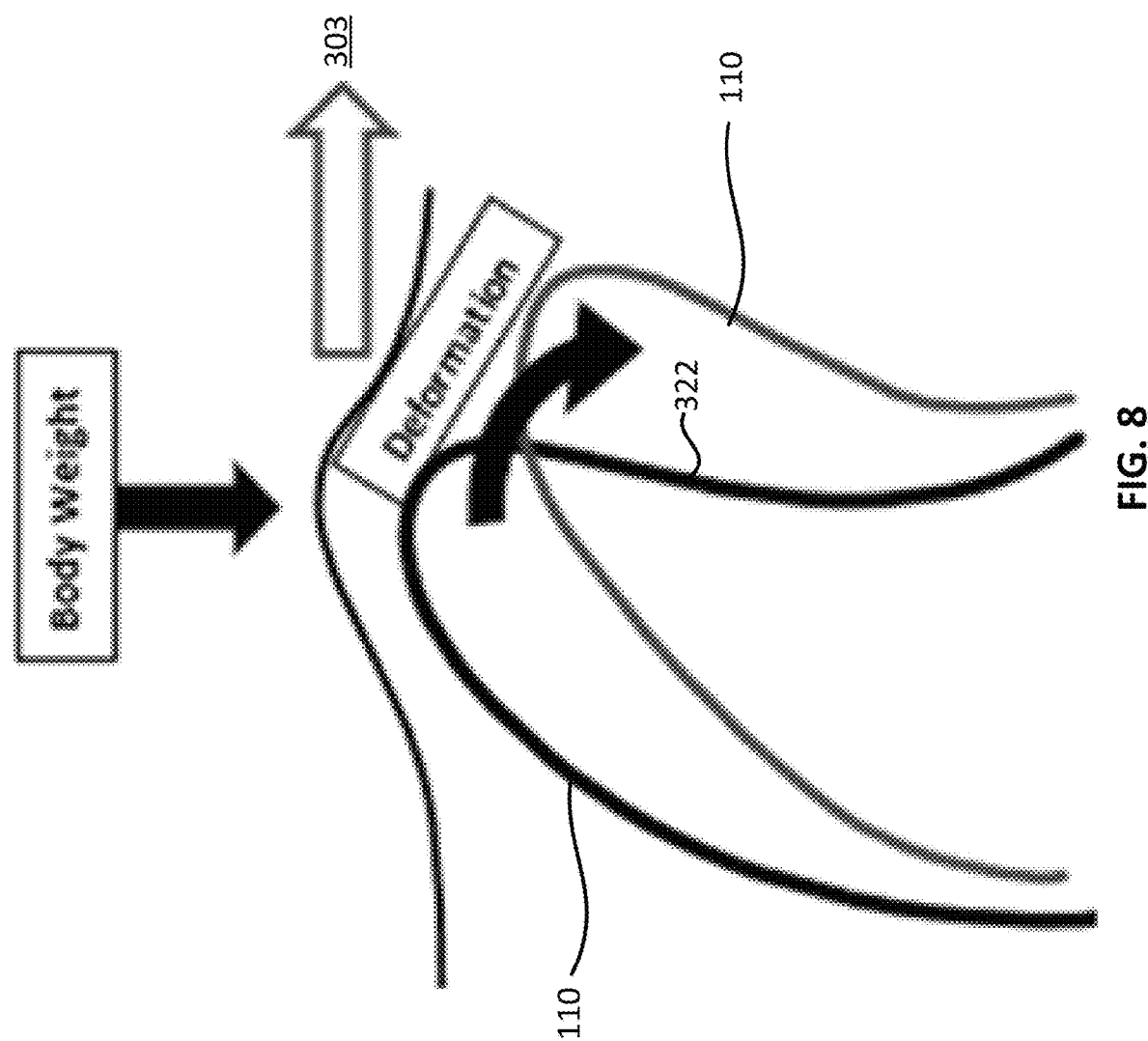
FIG. 8 schematically illustrates an example of crest deformation of an SI joint device when subjected to a load.

FIG. 8 illustrates deformation of a crest of an SI joint device when subjected to a load. Prior to being subjected to a load, the crest 110 can be upright, with a concavity 322 on a lateral side of the crest 110. A load, illustrated as a body weight, can then be applied to a top of the crest 110. The load may be applied when the SI joint device is positioned underneath a person and the crest 110 is aligned along an SI joint. As a result of the load, the crest 110 can deform towards a lateral end 303 of the SI joint device to pry open the SI joint and ligaments extending over the SI joint.

FIG. 9 is a flowchart of an embodiment of a process for treating SI joint hypomobility using an SI joint device. At block 902, a person can be positioned relative to an SI joint device (e.g., SI joint device 100). The SI joint device can include a resilient crest (e.g., resilient crest 110). Positioning the person relative to the SI joint device can involve aligning the resilient crest along an SI joint (e.g., SI joint 102) underneath the person. The SI joint device can include a body and a resilient cover positionable over a rigid protrusion of the body. The resilient crest may be defined by the rigid protrusion and the resilient cover. In some examples, the SI joint device may also include a vibration actuator positioned within the body.

At block 904, the SI joint device can be used to pry open the SI joint. As a load is applied to a top of the resilient crest, the resilient crest can deform towards a lateral end of the SI joint device to pry open the SI joint. Additionally, a lower surface of the body of the SI joint device can be curved to facilitate rocking of the SI joint device to further help to pry open the SI joint device. The SI joint device may be positioned at various locations along the SI joint with the resilient crest oriented at corresponding angles to release the SI joint and ligaments extending over the SI joint. In addition, once one SI joint of the person has been released, the SI joint device can be moved to the other SI joint of the person to pry open the other SI joint.

Specific details are given in the above description to provide an understanding of the embodiments. However, it is understood that the embodiments may be practiced without these specific details. In some instances, well-known processes, structures, and techniques may be shown without unnecessary detail in order to avoid obscuring the embodiments.

While the principles of the disclosure have been described above in connection with specific apparatus and methods, it is to be understood that this description is made only by way of example and not as limitation on the scope of the disclosure. Embodiments were chosen and described in order to explain the principles of the invention and practical applications to enable others skilled in the art to utilize the invention in various embodiments and with various modifications, as are suited to a particular use contemplated. It will be appreciated that the description is intended to cover modifications and equivalents.

The invention claimed is:

1. A method of treating sacroiliac (SI) joint hypomobility, the SI joint comprising a joint between a sacrum and ilium, the method comprising:
   positioning a person relative to a SI joint device, the SI joint device comprising a resilient crest, wherein positioning the person relative to the SI joint device comprises aligning the resilient crest along the SI joint underneath the person; and
   using the SI joint device to pry open the SI joint;
   wherein the SI joint device comprises a frame having a bottom member coupleable to a top member, wherein the bottom member comprises a crest-shaped protrusion extendable through an opening of the top member.

2. The method of claim 1, further comprising using the SI joint device to release one or more ligaments extending over the SI joint.

3. The method of claim 1, wherein the resilient crest is configured to deform towards the ilium as the resilient crest pries open the SI joint.

4. The method of claim 1, wherein an underside of the SI joint device includes a curved surface, wherein using the SI joint device to pry open the SI joint further comprises rocking the SI joint device.

5. The method of claim 4, wherein the SI joint device further comprises a vibration actuator, wherein using the SI joint device to pry open the SI joint further comprises vibrating the SI joint device.

6. The method of claim 1, wherein the resilient crest comprises a cover positionable over the crest-shaped protrusion, wherein the cover is more flexible than the frame.

7. The method of claim 1, further comprising:
using the SI joint device to pry open an anterior sacroiliac ligament, a posterior sacroiliac ligament, an interosseus ligament, a sacrotuberous ligament, a sacrospinous ligament and an iliolumbar ligament of the person.

8. The method of claim 1, wherein the SI joint is a first SI joint of the person and the method further comprises:
subsequent to using the SI joint device to pry open the first SI joint:
positioning the person relative to the SI joint device by aligning the resilient crest along a second SI joint underneath the person; and
using the SI joint device to pry open the second SI joint.

9. A sacroiliac (SI) joint device for treating SI joint hypomobility, the SI joint comprising a joint between a sacrum and ilium, the SI joint device comprising:
a body, the body extending between a medial end and a lateral end, the body comprising a rigid protrusion; and
a resilient cover extending over the rigid protrusion, the rigid protrusion and the resilient cover defining a crest configured to pry open an SI joint, the crest comprising a concavity oriented towards the lateral end of the body, the crest configured to deform towards the lateral end of the body when subjected to a load on a top of the crest.

10. The SI joint device of claim 9, wherein the body comprises an upper surface and a lower surface, wherein the rigid protrusion and the resilient cover are located at the upper surface, wherein the lower surface includes a curvature configured to facilitate rocking of the SI joint device.

11. The SI joint device of claim 9, wherein the crest extends along a generally superior-inferior axis of the SI joint device.

12. The SI joint device of claim 9, wherein the lateral end of the body is narrower than the medial end.

13. The SI joint device of claim 9, wherein the rigid protrusion comprises a crest-shape protrusion.

14. The SI joint device of claim 9, further comprises a vibration actuator configured to vibrate the SI joint device to pry open the SI joint.

15. The SI joint device of claim 14, wherein the vibration actuator is configured to be positioned within an internal cavity of the rigid protrusion.

16. The SI joint device of claim 15, wherein the body comprises a bottom cover configured to be positioned over the internal cavity.

17. The SI joint device of claim 9, wherein the body comprises a top member and a bottom member configured to be coupled via a coupling mechanism.

* * * * *